United States Patent [19]

Mayer

[11] 4,052,415
[45] Oct. 4, 1977

[54] MANUFACTURE OF LACTONES OF THE TRIPHENYLMETHANE SERIES

[75] Inventor: Kurt Mayer, Ludwigshafen, Germany

[73] Assignee: BASF Aktiengesellschaft, Ludwigshafen, Germany

[21] Appl. No.: 747,398

[22] Filed: Dec. 3, 1976

[30] Foreign Application Priority Data

Dec. 20, 1975 Germany .............................. 2557687

[51] Int. Cl.² .................... C07D 307/94; C09B 11/24; C07D 307/88
[52] U.S. Cl. ............................................... 260/343.4
[58] Field of Search ................... 260/343.4, 391, 618 B

[56] References Cited

U.S. PATENT DOCUMENTS 3,185,709  5/1965  Munro et al. ...................... 260/343.4

Primary Examiner—Lorraine A. Weinberger
Assistant Examiner—Jane T. Fan
Attorney, Agent, or Firm—Keil, Thompson & Shurtleff

[57] ABSTRACT

A process for the manufacture of

I

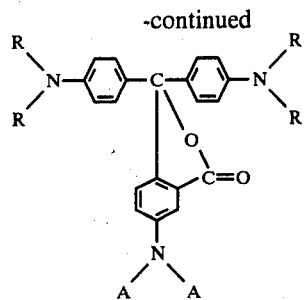

-continued where R and A are identical or different and each is alkyl of 1 to 4 carbon atoms, by oxidation of

II

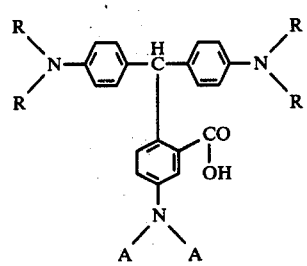

with air, oxygen or mixtures thereof, in an acid medium at a pH of from 1.5 to 5.5, at from 30° to 150° C. The reaction takes place rapidly and gives a good yield of the lactone (I), which can be freed from residual (II) by a treatment with alkali. The compound (I) is used as a dye intermediate in no-carbon copying systems.

10 Claims, No Drawings

MANUFACTURE OF LACTONES OF THE TRIPHENYLMETHANE SERIES

The present invention relates to a process for the manufacture of compounds of the general formula I

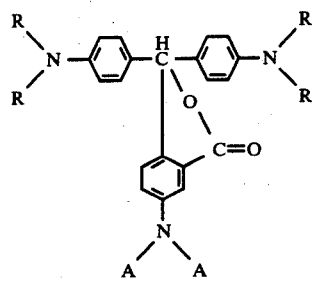

where R is alkyl of 1 to 4 carbon atoms and A is alkyl of 1 to 4 carbon atoms, and R and A may be identical or different, by oxidation of compound g of the formula II

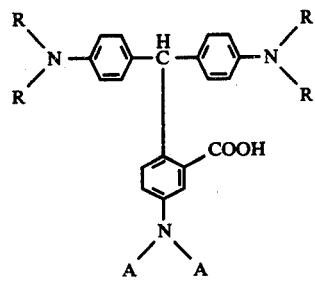

wherein the oxidation is carried out with air, oxygen or oxygen-containing gas mixtures in an acid medium.

R and A are, for example, n-propyl, iso-propyl or butyl, and especially ethyl and preferably methyl.

For the purposes of the present invention, acid media are mixtures of aromatic hydrocarbons with aliphatic carboxylic acids and in particular acid aqueous solutions which preferably contain an aliphatic carboxylic acid or aliphatic sulfonic acid.

The acid medium advantageously has a pH of from about 1.5 to 5.5, preferably from 2.0 to 3.5. This pH in the aqueous phase may be obtained by the use of the mineral acid, eg. sulfuric acid, hydrochloric acid or nitric acid, but the use of aliphatic carboxylic acids or aliphatic sulfonic acids, especially carboxylic acids of 1 to 4 carbon atoms or alkylsulfonic acids, where alkyl is of 1 to 4 carbon atoms, is preferred, since these compounds appear to act as solvents for the compounds of the formula II. In a purely organic medium, it is advantageous to use carboxylic acids.

In both media, carboxylic acids of 1 to 4 carbon atoms, eg. formic acid, butyric acid, haloacetic acids and particularly propionic acid and acetic acid are preferred.

Particularly preferred reaction media are mixtures of acetic acid and/or propionic acid and water which contain from 28 to 40% by weight of the carboxylic acids. In these media, the compounds II are oxidized rapidly without significant attack of the product, and the lactone is obtained in good yield and at the same time in good purity. If the reaction is carried out in water/acetic acid, a suitable starting material is, for example, a mixture of from about 200 to 300 parts by weight of a compound of the formula II, 800 parts by weight of acetic acid and 1,600 parts by weight of water. The ratios are not critical and may be varied within relatively wide limits. The most advantageous ratio of acid medium to compound of the formula II can easily be determined by preliminary experiments. In the case of the preferred acid media, the amount of carboxylic acid (II) is in general from 5 to 20% by weight, preferably from 10 to 16% by weight, based on the aqueous medium.

If the reaction is carried out in an organic phase, from about 300 to 400 parts of xylene and from 100 to 200 parts of acetic acid are used per 200 parts of the compound II. Here again, the ratios are not critical.

Oxidation catalysts, eg. Salcomin (a cobalt complex compound of the azomethine obtained from 1,2-diaminoethane and 2 moles of o-hydroxybenzaldehyde) may also be added to the reaction, but preferably the oxidation is carried out in the absence of such catalysts.

The oxidation according to the invention is advantageously carried out at elevated temperatures, above all at from 30° to 150° C, and preferably at from 60° to 90° C.

The reaction can be accelerated by pressure. This, however, at the same time causes oxidation of the lactone (ie. of the product), thereby reducing the yield. The oxidation is therefore advantageously carried out at atmospheric pressure.

If the air is replaced by oxygen, the reaction time is substantially shortened. However, in that case, as when working with air under pressure, the product I may undergo further oxidation.

The rate of reaction is furthermore determined by the stirrer used. If stirrers are used which divide the air into very fine bubbles in the reaction mixture, the reaction takes place substantially more rapidly than with stirrers which only distribute the air in the medium in the form of large bubbles.

In general, the reaction is complete in from 20 to 40 hours when carried out in water/carboxylic acid mixtures.

To isolate the lactone from the carboxylic acid/water mixtures, the reaction mixture is diluted, before filtration, by adding water or mixtures of water with methanol, ethanol and/or isopropanol, so that the content of aliphatic carboxylic acid is from 20 to 25%. The lactone is then separated off and washed neutral with water.

The product still contains some starting compound. The content of starting material can be reduced to less than 1% by weight by a simple aftertreatment with an alkali metal hydroxide or with sodium carbonate.

Using the process of the invention, the lactones of the formula I can be manufactured in good yield and good purity.

Compared to the process disclosed in U.S. Pat. No. 3,185,709 for the manufacture of compounds of the formula I, the new process possesses advantages in that the yield is better and the process is simpler to carry out.

The process according to the invention is further illustrated by the Examples which follow. Parts and percentages are by weight.

EXAMPLE 1

1,528 parts of air are passed, in the course of 50 hours, through a mixture of 300 parts of technical grade leucocrystal violet-o-carboxylic acid (2-(4,4'-bis-(dimethylamino)-benzhydryl)-5-dimethylaminobenzoic acid), corresponding to 260.4 parts of pure acid, 1,600 parts of water and 800 parts of glacial acetic acid whilst stirring at 80° C. The pH was 2.6 at the beginning and 2.8 at the end of the oxidation. The resulting suspension is cooled to room temperature and the product is filtered off. The filter residue which remains is washed neutral with water. After drying, 255 parts of a crystalline product having a melting point of 161°–164° C are obtained. According to a purity determination, this reaction product contains 229 parts of crystal violet-lactone (corresponding to 88.4% of theory) and 14 parts of leuco-crystal violet-o-carboxylic acid.

The proportion of the starting material can be lowered to less than 1% by a simple aftertreatment of the crude product with alkali. The crystal violet-lactone then obtained has a melting point of 174°–178° C.

EXAMPLE 2

200 parts of technical grade leuco-crystal violet-o-carboxylic acid, corresponding to 173.6 parts of pure acid, are stirred into 1,350 parts of water and 660 parts of glacial acetic acid. 1,172 parts of air are passed through the mixture in the course of 28 hours at 80° C, whilst stirring. The pH is 2.9 at the beginning of the reaction and 2.7 after the oxidation. The resulting suspension is worked up as described in Example 1. 142 parts of dry reaction product (melting point 166°–169° C) are obtained, containing 127 parts of crystal violet-o-carboxylic acid. If this starting material is removed by an aftertreatment at a pH of from 9 to 12, crystal violet-lactone of melting point 174°–178° C is obtained.

EXAMPLE 3

300 parts of technical grade leuco-crystal violet-o-carboxylic acid, containing 260.4 parts of pure acid, 1,600 parts of water and 800 parts of glacial acetic acid are heated at 80° C. 270 parts of oxygen are passed through the reaction mixture in the course of 6½ hours. The pH is 2.95 at the beginning of the reaction and 2.85 on completion of the oxidation. The resulting suspension is cooled and the product is filtered off. After washing neutral, and drying, 273 parts of reaction product of melting point 158°–168° C are obtained, containing 240 parts of crystal violet-lactone (92.6% of theory) and 15 parts of leuco-crystal violet-o-carboxylic acid. The starting material can be removed virtually completely by an alkaline aftertreatment at a pH of from 9 to 12.

EXAMPLE 4

The procedure described in Example 3 is followed, but only 200 parts of technical grade leuco-crystal violet-o-carboxylic acid, containing 173.6 parts of pure acid, are employed. The pH of the reaction mixture is 2.9 at the beginning of the oxidation and 2.8 at the end. 147 parts of reaction product (melting point 161°–163° C) are obtained, containing 138 parts of crystal violet-lactone (79.9% of theory) and 5.9 parts of leuco-crystal violet-o-carboxylic acid. The latter can be removed virtually completely by an aftertreatment at a pH of from 9 to 12.

EXAMPLE 5

200 parts of technical grade leuco-crystal violet-o-carboxylic acid, corresponding to 173.6 parts of pure acid, 1,050 parts of water and 530 parts of glacial acetic acid are heated at 80° C in a reaction vessel. The apparatus is flushed with oxygen and then sealed. An inlet tube is connected to a reservoir filled with oxygen. The reaction solution absorbs oxygen whilst being stirred. After 4½ hours, the absorption of oxygen has ended; 7.7 parts of oxygen are consumed. After having cooled to room temperature, the suspension obtained, which has a pH of 2.55, is filtered. The residual material is washed neutral with water and then dried. 161 parts of reaction product of melting point 163°–166° C are obtained. This product contains 144 parts of crystal violet-lactone, corresponding to a yield of 83.3% of theory, and 8 parts of leuco-crystal violet-o-carboxylic acid.

If the experiment is carried out in the absence of glacial acetic acid, a yield of only 17% of crystal violet-lactone is obtained.

EXAMPLE 6

The procedure followed is as in Example 5, but the oxidation is carried out at 90° C. The absorption of oxygen has ended after 5¼ hours; 6.5 parts of oxygen are consumed. The pH of the reaction mixture is 2.45. 160 parts of reaction product (melting point: 161°–163° C) are isolated, containing 143 parts of crystal violet-lactone (82.8% of theory) and 7.7 parts of leuco-crystal violet-o-carboxylic acid.

EXAMPLE 7

The procedure followed is as described in Example 5, but before the oxidation 5 parts of Salcomin (a cobalt complex compound obtained from 1,2-diaminoethane and 2 moles of 2-hydroxybenzaldehyde) are added to the reaction solution. The absorption of oxygen has ended after 5½ hours; 7.7 parts of oxygen are taken up. 161 parts of reaction product of melting point 156°–161° C are obtained. The product contains 144 parts of crystal violet-lactone (83.3% of theory) and 8.5 parts of leuco-crystal violet-o-carboxylic acid.

EXAMPLE 8

1,776 parts of air are passed, in the course of 44 hours, through a mixture of 300 parts of technical grade leuco-crystal violet-o-carboxylic acid, which contain 260.4 parts of pure acid, 1,800 parts of water and 88 parts of 8 percent strength aqueous hydrochloric acid at 80° C. The pH is 2.4 at the beginning and 2.5 at the end of the oxidation. The reaction suspension is then cooled to room temperature and filtered. The residue is washed neutral with water and dried. 179 parts of reaction product (melting point 142°–145° C), containing 89 parts of crystal violet-lactone (34.3% of theory) and 74.6 parts of leuco-crystal violet-o-carboxylic acid, are obtained.

Here again the content of starting material can be reduced to less than 1% by an alkaline aftertreatment.

EXAMPLE 9

300 parts of technical grade leuco-crystal violet-o-carboxylic acid, which contain 260.4 parts of pure acid, are heated, in 1,800 parts of water and 216 parts of 10 per cent strength sulfuric acid, at 80° C. 1,420 parts of air are passed through the reaction mixture in the course of 44 hours, whilst stirring. The pH of the reaction mixture is found to be 2.45 and 2.3 at the beginning and end of the oxidation, respectively. The resulting reaction product is filtered off at room temperature, washed neutral with water and dried. 250 parts of reaction product of melting point 138°–142° C are obtained. This material contains 161 parts of crystal violet-lactone (62.1% of theory) and 76 parts of leuco-crystal violet-o-carboxylic acid. The latter can be removed by treatment with alkali at a pH of from 9 to 12.

EXAMPLE 10

300 parts of technical grade leuco-crystal violet-o-carboxylic acid, which contain 260.4 parts of pure acid, in 2,100 parts of water and 305 parts of formic acid are stirred at 80° C. At this temperature, 1,528 parts of air are passed through the reaction mixture in the course of 47 hours. After cooling the mixture to 20°-25° C, the reaction product is isolated as described in the preceding Examples. The pH of the reaction mixture is found to be 2.4 at the beginning and 2.25 at the end of the oxidation. 148 parts of reaction product of melting point 156°-158° C are obtained, containing 87 parts of crystal violet-lactone (33.6% of theory) and 50 parts of leuco-crystal violet-o-carboxylic acid.

EXAMPLE 11

200 parts of technical grade leuco-crystal violet-o-carboxylic acid, which contain 173.6 parts of pure acid, in 1,050 parts of water and 530 parts of propionic acid are heated at 80° C. The mixture is oxidized with oxygen, whilst stirring, as described in Example 5. After 3 hours, the absorption of oxygen has ended and 8.1 parts of oxygen have been taken up. The pH determined both at the beginning and at the end of the reaction was 3.25. The resulting suspension is filtered at room temperature. The filtration residue is washed neutral with water, and dried. 146 parts of product of melting point 167°-169° C are obtained, containing 134 parts of crystal violet-lactone (77.5% of theory) and 8 parts of leuco-crystal violet-o-carboxylic acid.

EXAMPLE 12

300 parts of technical grade leuco-crystal violet-o-carboxylic acid, which contain 260.4 parts of pure acid, are heated in 1,600 parts of water and 800 parts of glacial acetic acid at 80° C. The mixture is oxidized with 710 parts of air under 2.8 atmospheres gauge pressure in the course of 20 hours, whilst stirring. After cooling, and letting down the reaction vessel, 251 parts of reaction product (melting point: 162°-166° C) are isolated, containing 218 parts of crystal violet-lactone (84.1% of theory) and 10 parts of leuco-crystal violet-o-carboxylic acid. The latter can be removed by an alkaline aftertreatment at a pH of from 9 to 12.

EXAMPLE 13

400 parts of technical grade leuco-crystal violet-o-carboxylic acid, which contain 347.2 parts of pure acid, are heated in 690 parts of xylene and 200 parts of glacial acetic acid at 80° C. 286 parts of oxygen are passed through the reaction mixture in the course of 7 hours whilst stirring. The resulting reaction solution is cooled to room temperature and then neutralized with aqueous ammonia solution. After adding methanol, the product which has precipitated becomes crystalline. It is filtered off and washed with methanol and water. After drying, 102.5 parts of reaction product of melting point 172°-174° C are obtained, containing 95.7 parts of crystal violet-lactone (27.7% of theory) and 1.2 parts of leuco-crystal violet-o-carboxylic acid.

I claim:

1. A process for the manufacture of compounds of the formula

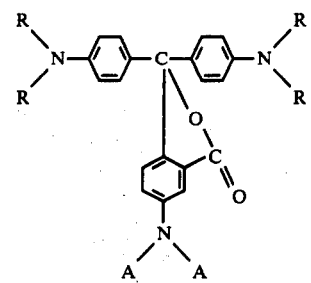

where R is alkyl of 1 to 4 carbon atoms and A is alkyl of 1 to 4 carbon atoms, and R and A may be identical or different, wherein compounds of the formula

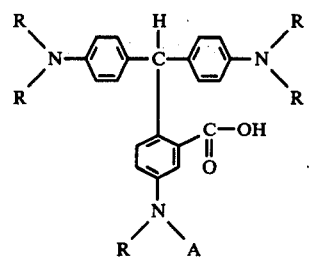

are oxidized with air, oxygen or oxygen-air mixtures in an acid medium, at a pH of from 1.5 to 5.5, in the presence or absence of oxidation catalysts, at from 30° to 150° C.

2. A process as claimed in claim 1, wherein the oxidation is carried out in an acid medium at a pH of from 2.0 to 3.5.

3. A process as claimed in claim 1, wherein mixtures of water and carboxylic acids of 1 to 4 carbon atoms are used as the acid medium.

4. A process as claimed in claim 1, wherein a mixture of water with formic acid, propionic acid, acetic acid or their mixtures is used as the acid medium, the said aqueous mixture containing from 28 to 40% by weight of the carboxylic acids, based on the medium.

5. A process as claimed in claim 4, wherein the oxidation is carried out with air at atmospheric pressure.

6. A process as claimed in claim 2, wherein the oxidation is carried out in the absence of oxidation catalysts.

7. A process as claimed in claim 4, wherein the oxidation is carried out in the absence of oxidation catalysts.

8. A process as claimed in claim 1, wherein the oxidation is carried out at from 60° to 90° C.

9. A process as claimed in claim 1, wherein a compound of the formula

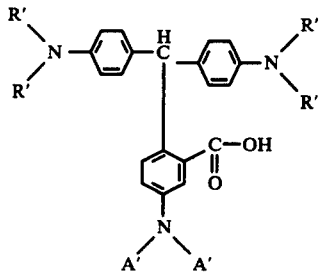

where R' and A' are methyl or ethyl, is oxidized.

10. A process for the manufacture of the compound of the formula

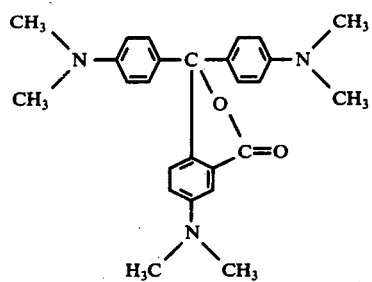
wherein the compound of the formula
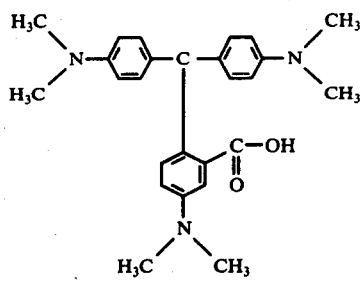
is oxidized with air at atmospheric pressure, in aqueous acetic acid, aqueous propionic acid or mixtures thereof, which contain from 28 to 40% by weight, based on the solution, of acetic acid, propionic acid or both carboxylic acids, at from 60° to 90° C.
* * * * *

UNITED STATES PATENT AND TRADEMARK OFFICE
CERTIFICATE OF CORRECTION

PATENT NO. : 4,052,415

DATED : October 4, 1977

INVENTOR(S) : MAYER, KURT

It is certified that error appears in the above-identified patent and that said Letters Patent are hereby corrected as shown below:

In the Abstract, second line after formula I, delete "alky" and substitute --alkyl--.

In claim 1, second formula in column 6, delete " 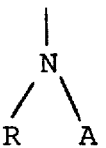 " and substitute -- 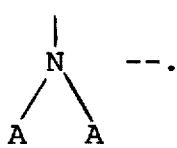 --.

Signed and Sealed this

Seventeenth Day of April 1979

[SEAL]

Attest:

RUTH C. MASON
*Attesting Officer*

DONALD W. BANNER
*Commissioner of Patents and Trademarks*